(12) United States Patent
Aehle (10) Patent No.: US 10,265,096 B2
(45) Date of Patent: Apr. 23, 2019

(54) TUNNELING TOOL AND METHOD FOR AN IMPLANTABLE MEDICAL LEAD EXTENSION

(71) Applicant: Medtronic, Inc., Minneapolis, MN (US)

(72) Inventor: Matthew A. Aehle, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 197 days.

(21) Appl. No.: 14/210,839

(22) Filed: Mar. 14, 2014

(65) Prior Publication Data

US 2014/0276930 A1    Sep. 18, 2014

Related U.S. Application Data

(60) Provisional application No. 61/781,730, filed on Mar. 14, 2013.

(51) Int. Cl.
*A61B 17/34* (2006.01)
*A61N 1/05* (2006.01)
(Continued)

(52) U.S. Cl.
CPC ........ *A61B 17/3468* (2013.01); *A61N 1/0551* (2013.01); *A61N 1/36017* (2013.01);
(Continued)

(58) Field of Classification Search
CPC ...... A61B 2017/3458; A61B 2017/349; A61B 17/3468; A61B 2017/320052; A61B 2017/320044; A61B 1/00131; A61B 1/012; A61B 1/00101; A61B 1/0008; A61B 1/00089; A61B 1/00091; A61B 1/00073; A61B 1/00137; A61B 1/00142; A61B 1/00103; A61B 1/00075; A61B 1/00135;
(Continued)

(56) References Cited

U.S. PATENT DOCUMENTS 5,092,848 A * 3/1992 deCiutiis ........... A61M 25/0069
604/170.01
5,271,380 A * 12/1993 Riek .................. A61B 1/00165
600/104

(Continued)

OTHER PUBLICATIONS

Implant Manual, 1x8 Low Impedance Extension Kit, 37081, p. 1-10, Mar. 2005.
Sepple, "Tunneing Tool Accessory Kit", 3655, Oct. 21, 2005.

*Primary Examiner* — Christopher L Templeton
(74) *Attorney, Agent, or Firm* — Withers & Keys, LLC (57) ABSTRACT

A tunneling tool is used to create a subcutaneous tunnel for passage of a lead extension. The lead extension is transported from a proximal incision site to a distal incision site and as a result the proximal connector of the lead extension does not pass through the subcutaneous tunnel. The tunneling tool may carry the lead extension during the tunneling procedure. The tunneling tool may include a tool body that contains the lead extension as the lead extension is being carried to the distal incision site. The tunneling tool may further include a tracker tube that is present within the tool body, and the lead extension is contained in and carried by the tracker tube.

8 Claims, 9 Drawing Sheets

(51) Int. Cl.
*A61M 25/01* (2006.01)
*A61N 1/36* (2006.01)
*A61B 17/32* (2006.01)

(52) U.S. Cl.
CPC ............... *A61N 1/36021* (2013.01); *A61B 2017/320056* (2013.01); *A61M 25/0194* (2013.01); *A61N 1/056* (2013.01); *A61N 1/0587* (2013.01); *A61N 2001/058* (2013.01)

(58) Field of Classification Search
CPC ...... A61B 1/0125; A61B 1/0055; A61N 1/05; A61N 1/0592; A61N 1/056; A61N 1/0587; A61N 2001/058; A61M 25/0069; A61M 25/06; A61M 25/0068; A61M 25/0067; A61M 25/0194; A61M 25/0662; A61M 25/065; A61M 25/3415; A61M 2025/0197
USPC ............... 606/129; 604/164.01, 44, 533, 528
See application file for complete search history.

(56) References Cited

U.S. PATENT DOCUMENTS

| | | | | |
|---|---|---|---|---|
| 5,591,192 A * | 1/1997 | Privitera | ............ | A61B 1/00087 600/114 |
| 5,685,820 A * | 11/1997 | Riek | ............ | A61B 1/00165 600/104 |
| 5,817,061 A * | 10/1998 | Goodwin | ............ | A61B 17/3417 600/121 |
| 6,241,738 B1 * | 6/2001 | Dereume | ............ | A61B 17/00234 606/108 |
| 6,605,094 B1 | 8/2003 | Mann et al. | | |
| 7,384,423 B1 * | 6/2008 | Chin | ............ | A61B 17/00008 606/190 |
| 7,470,230 B2 * | 12/2008 | Smith | ............ | A61B 17/34 600/184 |
| 2005/0085694 A1 * | 4/2005 | Nakao | ............ | A61B 1/00073 600/153 |
| 2005/0288762 A1 * | 12/2005 | Henderson | ............ | A61B 17/3415 623/1.11 |
| 2006/0009783 A1 * | 1/2006 | Rome | ............ | A61B 17/3415 606/108 |
| 2006/0271032 A1 * | 11/2006 | Chin | ............ | A61B 18/1482 606/41 |
| 2007/0106113 A1 * | 5/2007 | Ravo | ............ | A61B 1/00073 600/113 |
| 2007/0129719 A1 * | 6/2007 | Kendale | ............ | A61B 1/00096 606/41 |
| 2007/0282274 A1 * | 12/2007 | Chesnin | ............ | A61B 17/3415 604/175 |
| 2008/0214992 A1 * | 9/2008 | Haarala | ............ | A61B 17/3415 604/44 |
| 2009/0048486 A1 * | 2/2009 | Surti | ............ | A61B 1/0008 600/127 |
| 2009/0137944 A1 * | 5/2009 | Haarala | ............ | A61M 25/0194 604/44 |
| 2012/0078086 A1 * | 3/2012 | Hoffa | ............ | A61B 10/0275 600/424 |
| 2012/0083794 A1 * | 4/2012 | Martin | ............ | A61B 17/3415 606/108 |
| 2012/0290064 A1 * | 11/2012 | Fargahi | ............ | A61M 25/0069 623/1.11 |
| 2014/0018737 A1 * | 1/2014 | Chebator | ............ | A61M 25/0194 604/164.01 |
| 2014/0066854 A1 * | 3/2014 | Martin | ............ | A61B 17/320016 604/164.01 |
| 2014/0088564 A1 * | 3/2014 | Augustine | ............ | A61B 17/3415 604/528 |
| 2014/0350343 A1 * | 11/2014 | Kim | ............ | A61B 1/07 600/121 |

\* cited by examiner

TUNNELING TOOL AND METHOD FOR AN IMPLANTABLE MEDICAL LEAD EXTENSION

RELATED APPLICATIONS

The present application claims priority to U.S. Provisional Application No. 61/781,730, filed on Mar. 14, 2013, and entitled TUNNELING TOOL AND METHOD FOR AN IMPLANTABLE MEDICAL LEAD EXTENSION, the entire contents of which are incorporated by reference herein.

TECHNICAL FIELD

Embodiments are related to tunneling tools for implantable medical lead extensions. More particularly, embodiments are related to tunneling tools that carry the implantable medical lead extension while tunneling.

BACKGROUND

When a patient is a candidate for stimulation therapy such as sacral nerve stimulation or spinal cord stimulation therapy to treat incontinence, chronic pain, or related conditions, it is often desirable to conduct a trial period of stimulation. This trial period allows an external stimulator to be used so that the patient is not required to undergo a full stimulation device implantation procedure. If the trial is successful, then an implantable stimulator is fully implanted into the patient.

When implanting the trial system, an implantable medical lead is implanted with a distal end being routed to the stimulation site. An implantable lead extension is typically then routed subcutaneously from the location of the proximal end of the implanted medical lead to an exit site nearby the location where the external device will be mounted to the patient. In some cases, an external lead is then used to interconnect the exposed proximal end of the implantable lead extension to the external device. In other cases, the exposed proximal end of the implantable lead extension is connected directly to the external device.

To route the implantable lead extension, a subcutaneous tunnel is first created between the exit site nearby the position of the external device and the location of the proximal end of the implanted lead. A physician uses a tunneling tool to create the tunnel. The physician then loads the proximal end of the lead extension into a carrier of the tunneling tool and retracts the tunneling tool back through the tunnel to thereby pull the lead extension through the tunnel. The tunneling tools for this approach may be adequate for lead extensions having proximal connectors that are relatively small, such as where an external lead will be used to connect the lead extension to the external device. However, the conventional tunneling tools that utilize this approach are impractical in other situations. For instance, conventional tunneling tools may not be effective where the lead extension has a relatively large proximal connector such as where the proximal connector connects directly to the external device.

SUMMARY

Embodiments address issues such as these and others by providing tunneling tools and methods where the tunneling tool carries a distal connector of the lead extension while the tunneling is being performed. Using this approach, the proximal connector of the lead extension does not pass through the subcutaneous tunnel but remains external to the body of the patient during the implantation procedure.

Embodiments provide a method of implanting a lead extension. The method involves inserting a distal connector and at least a portion of a body of the lead extension into a tool body of the insertion tool. While the distal connector and at least the portion of the body of the lead extension are positioned within the tool body, the method further involves tunneling with the lead insertion tool subcutaneously to pass the distal connector from a first incision site to a second incision site.

Embodiments provide a tunneling tool for implanting a lead extension. The tunneling tool includes a tool body having a lumen sized to allow passage of a body and proximal and distal connectors of the lead extension and a handle attached to a proximal end of the tool body. The handle has a passageway that is sized to receive a portion of the body of the lead extension. The tunneling tool also includes a distal cap that is removably attached to a distal end of the tool body and a tracker tube having a distal compartment sized to receive and carry a distal connector of the lead extension while a body of the lead extension is present within the lumen and passageway. The tracker tube is contained within the lumen of the tool body and with the distal compartment being positioned in proximity to the distal end of the tool body.

Embodiments provide a system that includes a lead extension having a lead body, a proximal connector, and a distal connector. The system also includes a tool body having a lumen with a portion of the body and the proximal connector being present within the tool body. The handle is attached to a proximal end of the tool body, and the handle has a passageway with a portion of the body of the lead extension being positioned in the passageway. The system further includes a distal cap that is removably attached to a distal end of the tool body and a tracker tube that has a distal compartment where the distal connector of the lead extension is positioned while a body of the lead extension is present within the lumen and passageway. The tracker tube is contained within the lumen of the tool body and with the distal compartment being positioned in proximity to the distal end of the tool body.

DETAILED DESCRIPTION

Embodiments of a method and tunneling tool as well as a system including a lead extension that is at least partially implantable and that is loaded within the tunneling tool allow the lead extension to be carried by the tunneling tool while the tunneling tool is creating the tunnel. The tunneling tool carries the distal end of the lead extension such that a proximal connector of the lead extension remains external to the subcutaneous tunnel.

Figure 1A:
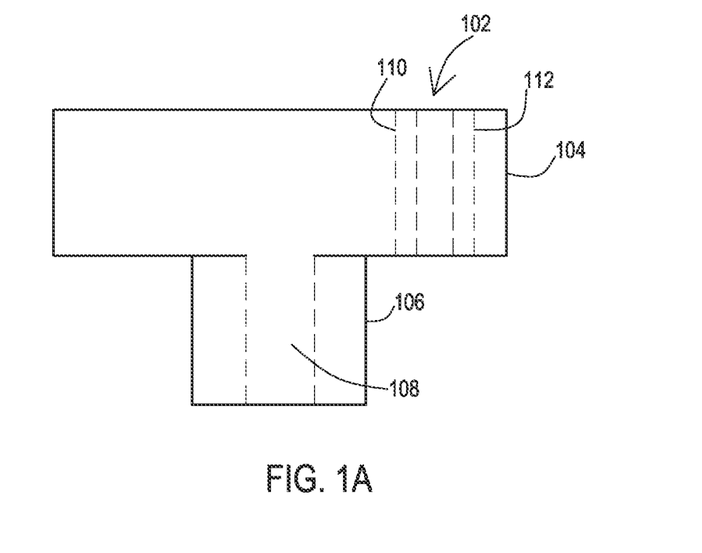
FIGS. 1A and 1B show views of an example of a handle for various embodiments of a tunneling tool.
Figure 1B:
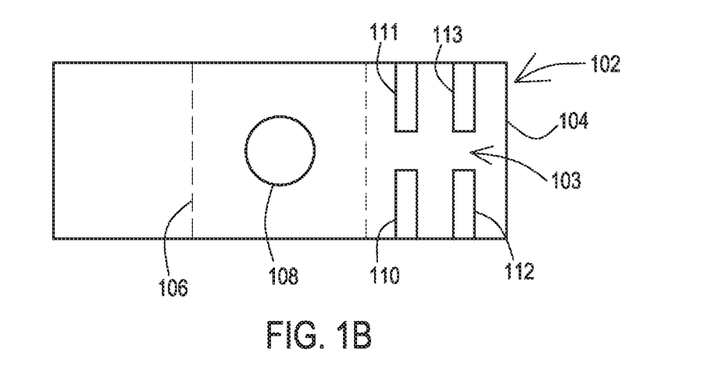

FIGS. 1A and 1B show an example of a handle 102 that may be included for the tunneling tool. The handle 102 provides a proximal end of the tunneling tool that the physician may grasp when forcing the tunneling tool to create the subcutaneous tunnel as well as when retracting the tunneling tool. The handle 102 includes a wide portion 104 and a narrower neck portion 106. The narrower neck portion is used to connect the handle 102 to a body of the tunneling tool which is discussed in more detail below with reference to FIG. 2. However, it will be appreciated that the handle 102 and the body may instead be constructed as a single unit.

The handle 102 includes various features to aid in carrying the lead extension when tunneling. While the handle 102 may be hollow and include a passageway 108 that extends through the neck portion 108, this example of the handle 102 includes vertical spars 110, 111, 112, and 113. These spars form a channel 103 that can accept and hold the lead extension and a tracker tube that surrounds the lead extension during tunneling to thereby prevent the lead extension from interfering with the ability of the physician to grasp the wide portion 104 of the handle 102. The tracker tube is discussed below in more detail with reference to FIGS. 3 and 4.

Figure 2:
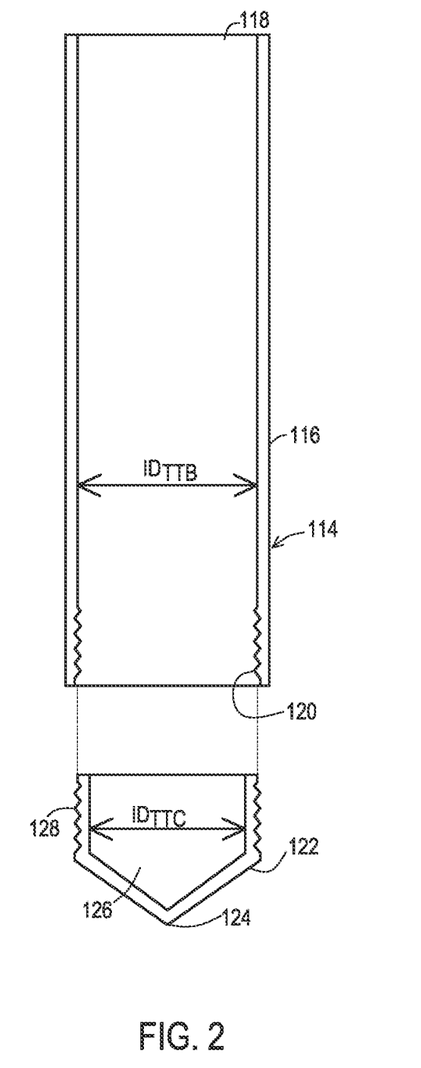
FIG. 2 shows an example of a tool body and distal cap for various embodiments of a tunneling tool.

FIG. 2 shows a cross-sectional view of the tool body 114 and distal cap 122. The tool body 114 includes a tubular structure 116 that defines a lumen 118. The proximal end of the tubular structure 116 attaches to the neck portion 106 of the handle 102 in this example. As discussed above, in other examples the tool body 114 and handle 102 may be formed as a single unit. The distal end includes threads 120 that engage threads 128 of the distal cap 122 when the distal cap 122 is installed on the tubular structure 116. The distal cap 122 can be attached and removed from the tubular structure 116 by rotation to tighten and loosen the threaded engagement.

In this example, the tubular structure 116 has an inside diameter, $ID_{TTB}$, while the distal cap 122 has an inside diameter $ID_{TTC}$, where $ID_{TTC}$ is slightly smaller considering the threaded end of the distal cap 122 fits inside the threaded distal end of the tool body 114. These diameters are related to the diameters of the various components that pass through the tubular structure 116 as described below.

The distal cap 122 performs various functions. The distal cap 122 provides the tissue piercing function during the tunneling via a pointed tip 124. Additionally, the distal cap of this example carries and stabilizes a distal end of the tube tracker during the tunneling via a conical interior compartment 126.

Figure 3:
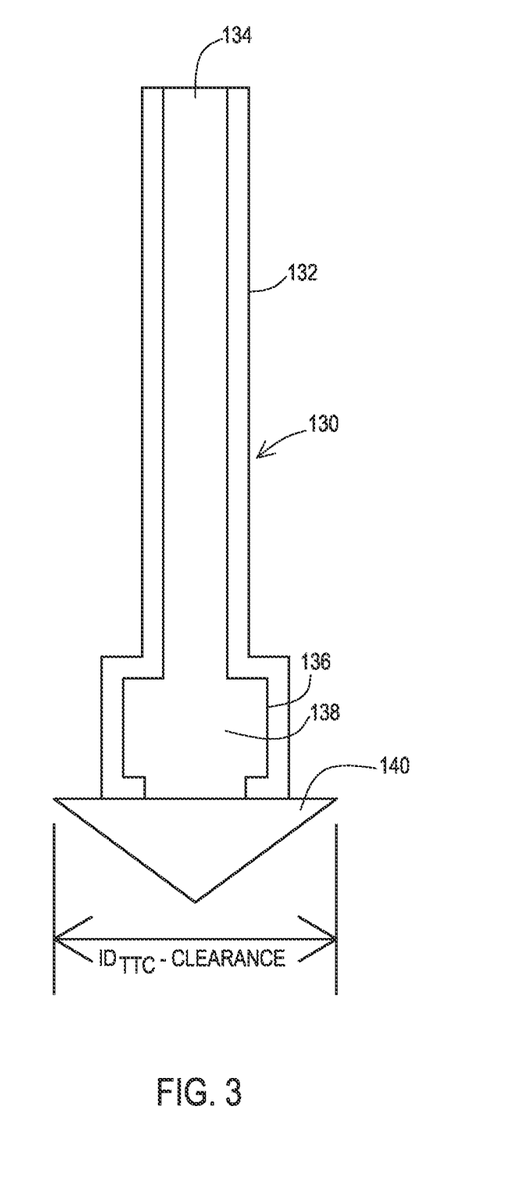
FIG. 3 shows an example of a tracker tube for various embodiments of a tunneling tool.
Figure 4:
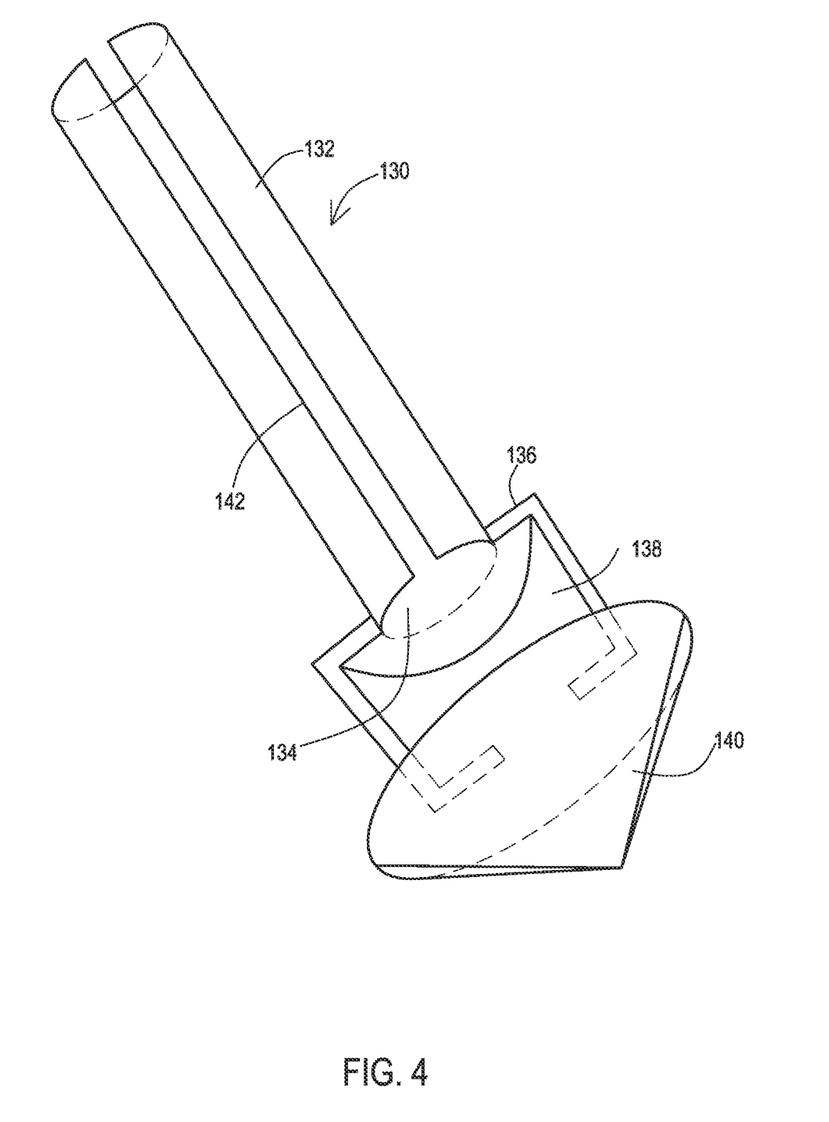
FIG. 4 shows a perspective view of the tracker tube.

FIG. 3 shows a cross-section and FIG. 4 shows a perspective view of an example of a tracker tube 130. The tracker tube 130 includes a tubular portion 132 that defines a lumen 134. The tracker tube 130 also includes a widened portion 136 that defines a distal compartment 138 on the distal end of the tubular portion 132. This example of the tracker tube 130 also includes a conical distal end 140 having a diameter that is less than $ID_{TTC}$ by some amount of clearance to allow the conical distal end to be situated in the conical interior compartment 126 of the distal cap 122.

The distal compartment 138 of the tracker tube 130 receives the distal connector of the lead extension to carry the lead extension while tunneling subcutaneously. The body of the lead extension then extends through the lumen 134. The tube tracker 130 extends through the lumen 118 of the tool body 114. To assist in removing the lead extension from the tracker tube 130 during the implantation procedure, the tubular structure 132 also includes a longitudinal slot 142 that allows the body of the lead extension to be removed in a lateral direction.

Figure 5:
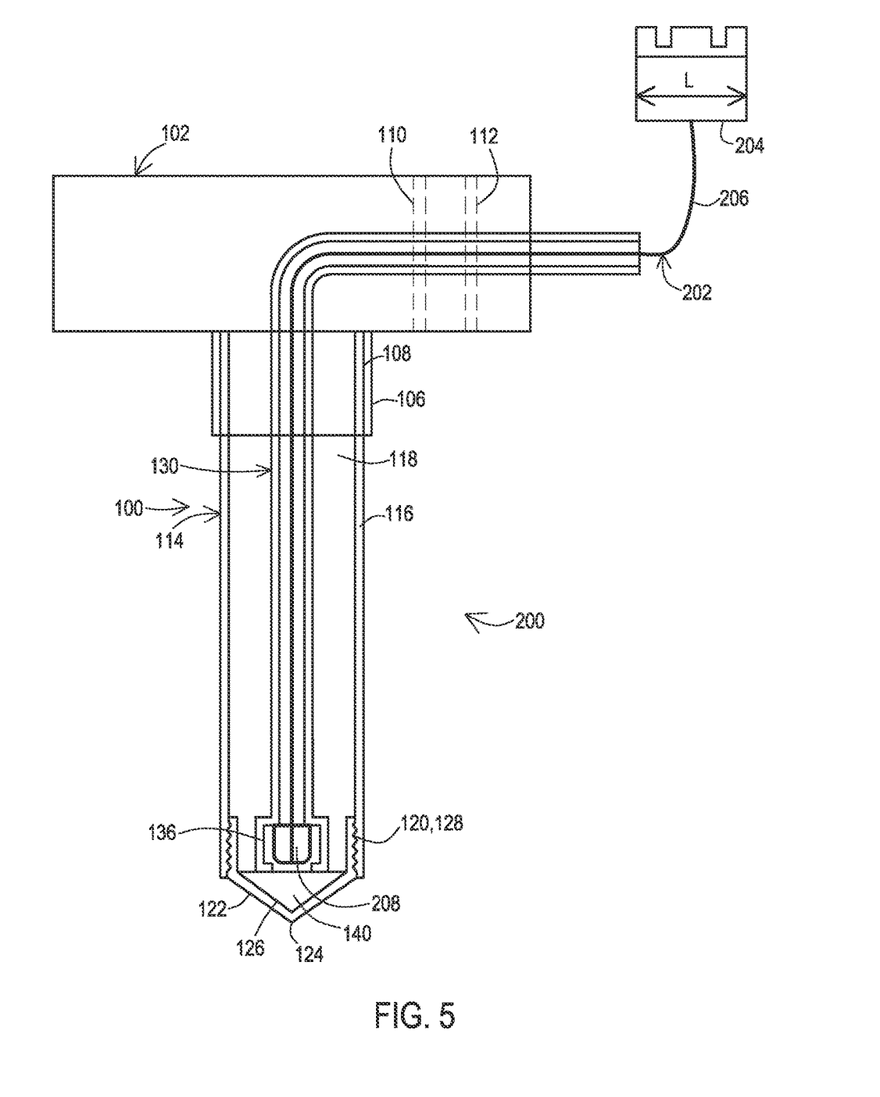
FIG. 5 shows a system including an example of a tunneling tool and an example of a lead extension positioned within the tunneling tool.

FIG. 5 shows a cross-section of a system 200 that includes the assembled tunneling tool 100 having the handle 102, tool body 114 with distal cap 122, and the tracker tube 130. The system 200 also includes an implantable lead extension 202 positioned within the assembled tunneling tool 100. The lead extension 202 has a proximal end having a proximal connector 204. A lead extension body 206 extends from the proximal connector 204 to a distal connector 208.

The proximal connector 204 of this example is designed to connect direction to an external stimulation device and is designed to be grasped by the physician and plugged into the external device. Therefore, the proximal connector 204 is substantially larger than the distal connector 208. The proximal connector 204 has a width, L, that is smaller than $ID_{TTB}$ to provide clearance for passing through the lumen 118 of the tool body 114, and hence the passageway 108 of the handle 102, during removal of the tunneling tool 100.

As shown in FIG. 5, the lead extension 202 is contained within the tracker tube 130 which together pass through the slot 103 of the handle 102 and through the lumen 118. The distal connector 208 is positioned within the compartment 138 while the conical tip 140 is positioned within the conical interior of the distal cap 122.

The components of the tunneling tool 100 may be constructed of various materials. The handle 102, tool body 114, and distal cap 122 may be constructed of rigid materials such as biocompatible metals like stainless steel. The tool body 114 may be constructed of a material that allows the physician to create bends that assist in steering the tunneling tool 100 while remaining adequately stiff to allow the tool 100 to be forced subcutaneously while the distal cap 122 pierces the tissue. The tracker tube 130 may be constructed of a flexible material such as a biocompatible polymer.

Figure 6:
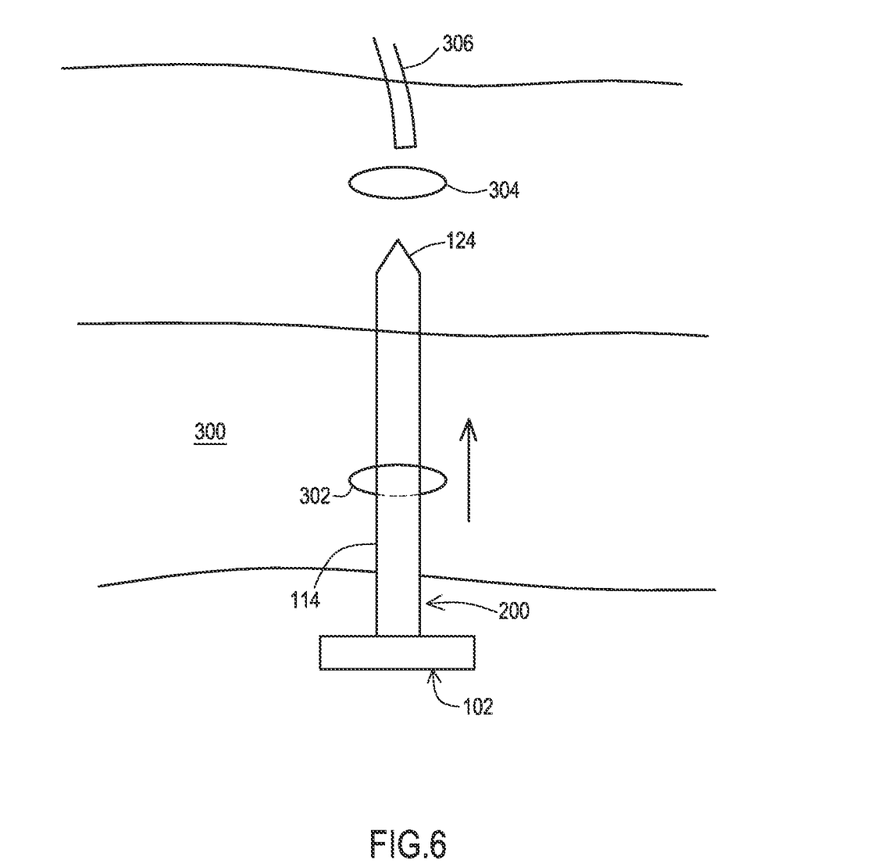
FIG. 6 shows the system where the tunneling tool is being forced to produce the subcutaneous tunnel while carrying the lead extension.

FIG. 6 shows the system 200 during the tunneling procedure. A body 300 of a patient has a first incision 302 where it is desirable for the implantable lead extension to exit the body. The body 300 has a second incision 304 where it is desirable to implant a medical lead 306. The system 200 includes the lead extension 202 positioned within the tunneling tool 100. The physician inserts the distal tip of the tool 100 into the first incision 302 and then applies force to the handle 102 to tunnel subcutaneously from the incision 302 to the incision 304 where the distal tip 122 becomes exposed to thereby deliver the distal connector 208 of the lead extension to the location where the proximal end of the lead 306 is located.

Figure 7:
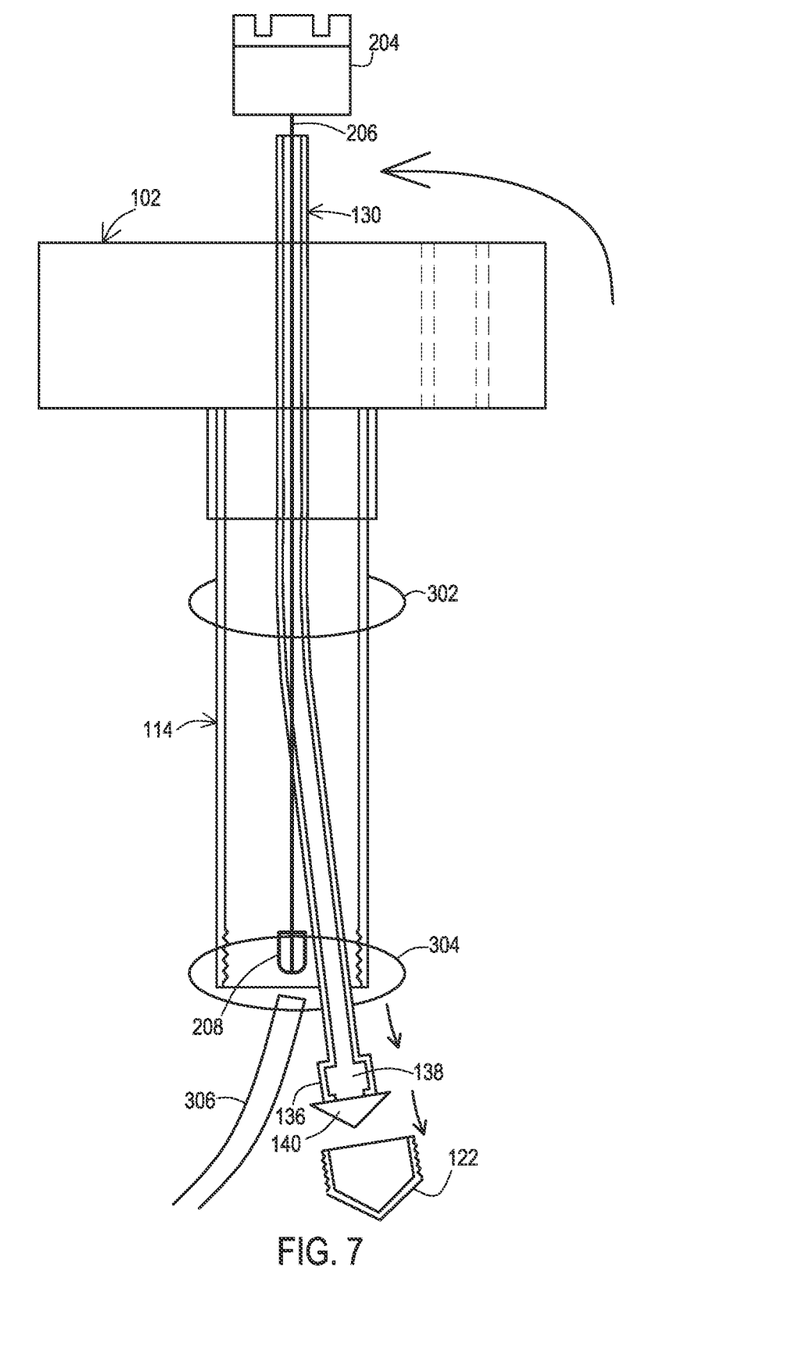
FIG. 7 shows the removal of the tracker tube from the subcutaneous tunnel in the distal direction while the lead extension remains extended through the tool body in the subcutaneous tunnel.
Figure 8:
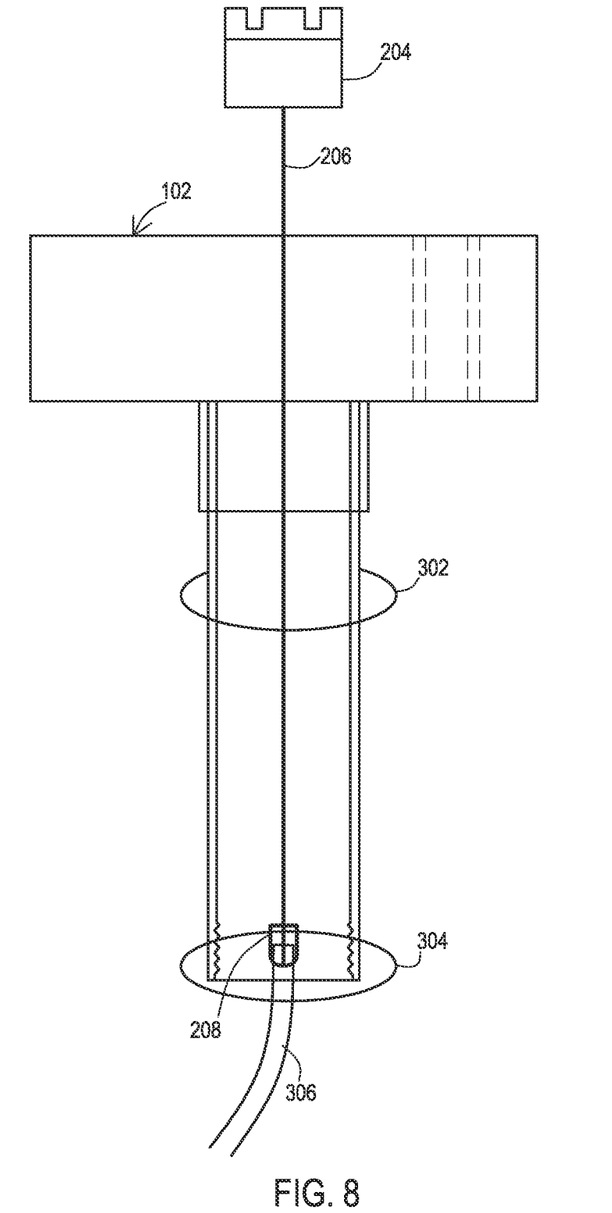
FIG. 8 shows interconnection of the lead extension to the implanted lead while the lead extension remains extended through the tool body in the subcutaneous tunnel.
Figure 9:
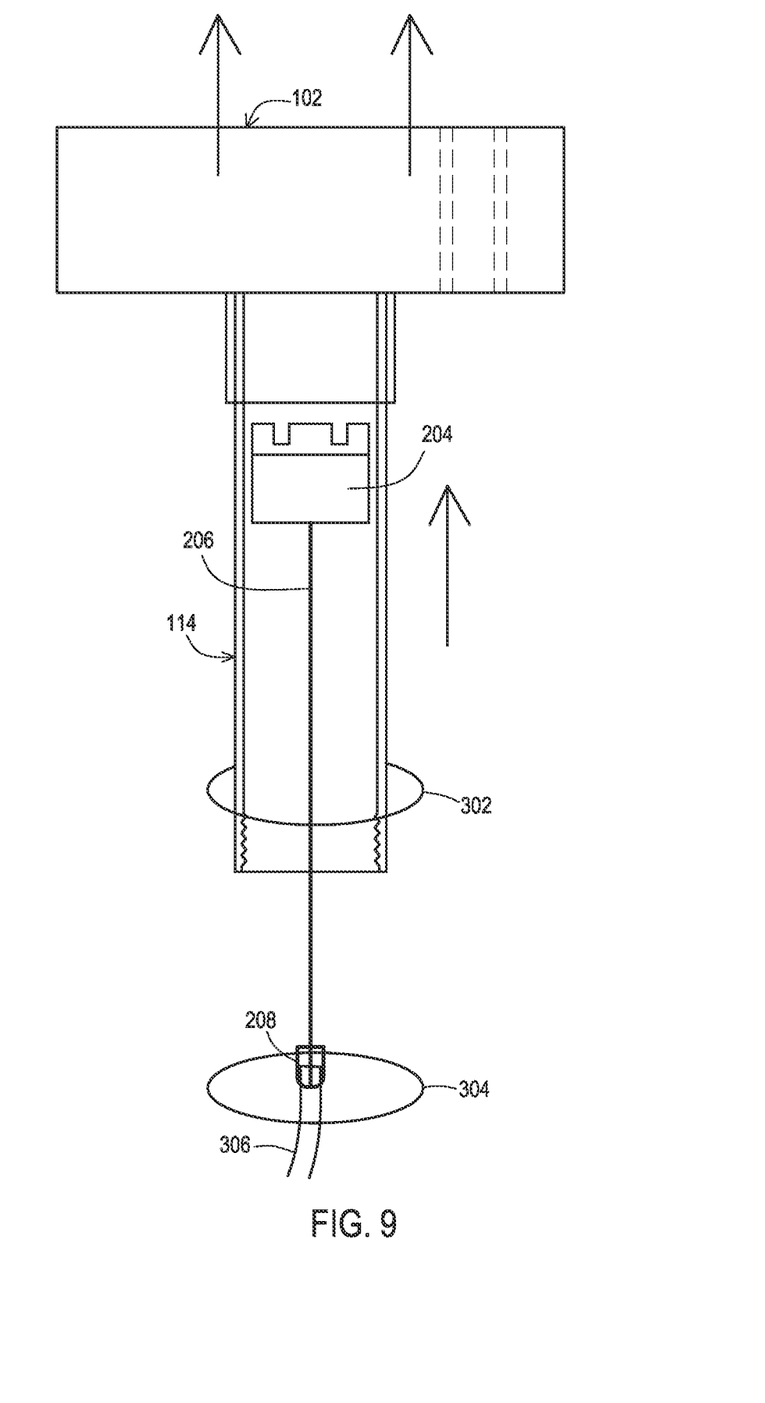
FIG. 9 shows the removal of the tool body from the subcutaneous tunnel in the proximal direction while the lead extension remains extended through the subcutaneous tunnel.

FIGS. 7-9 show an example of stages for removing the tunneling tool 100. In FIG. 7, at the incision site 304, the distal tip 122 may be removed to expose the distal end of the tracker tube 130 and also expose the distal connector 208. The distal connector 208 is removed from the compartment 138 of the tracker tube 130. The tracker tube 130 and lead extension 202 are then removed from the slot 103 of the handle 102 so that the tracker tube 130 is not restrained. Then the lead extension body 206 is removed from the tracker tube 130 by lateral movement of the tracker tube 130 and/or lead extension 202 to allow the lead extension 202 to exit the tracker tube 130 through the slot 142. The tracker tube 130 is also being pulled longitudinally in the distal direction out of the lumen 118 and out through the incision site 304.

As shown in FIG. 8, the distal connector 208 of the lead extension 202 is then fully exposed at the incision site 304. The distal connector 208 is then connected to the proximal end of the implanted lead 306 at the incision site 304. Also at this point, the lead extension 202 is positioned so that the remainder of the tunneling tool 100 may be removed in the proximal direction.

FIG. 9 shows the removal of the remainder of the tunneling tool 100. The physician pulls the handle 102 in the proximal direction while allowing the lead extension body 206 and proximal connector 204 to feed through the hole 108 of the handle 102 and the lumen 118 of the tool body 114. The tool body 114 exits proximally through the incision site 302 and the proximal connector 204 then exits through the distal end of the tool body 114. The proximal connector 204 can then be connected to an external stimulation device to complete the stimulation path from the external stimulation device to the implanted lead 306.

As can be seen, during this approach, the proximal connector 204 was not required to pass through the subcutaneous tunnel between incisions 302 and 304. Furthermore, because the lead extension was transported through the subcutaneous tunnel prior to removal of the tool body 114, there is nothing to be attached to the tool body 114 prior to retracting the body 114 through the subcutaneous tunnel. Additionally, while this procedure is shown as having the lead extension be carried during the tunneling, other techniques are also possible using embodiments of the tunneling tool 100. For instance, the tunneling tool 100 can be used to create the tunnel prior to installation of the lead extension 202 and tracker tube 130 and then the lead extension 202 and tracker tube 130 can be fed through the lumen 118 to deliver the distal end of the lead extension to the location of the lead 306 at the incision site 304.

Furthermore, variations in the tunneling tool 100 may be utilized. As one example, the handle 102 may instead be of other shapes and configurations such as a gripping surface formed about the proximal end of the tool body 114 rather than having a T-shape as shown. As another example, the conical tip 140 may be omitted from the tracker tube 130. However, including the conical tip 140 provides the physician with a tactile feedback once the tip 140 is engaged with the distal cap 122 which reassures the physician that the tracker tube 130 with the lead extension 202 are properly loaded into the tunneling tool 100. Additionally, the tracker tube 130 may be omitted from the tunneling tool 100 with the lead extension 202 being placed directly inside the lumen 118 of the body 114 either before or after the tool 100 is used to pierce the tissue and create the tunnel, although the tracker tube 130 provides the physician with a reassurance that the lead extension 202 is being safely transported and will be easily accessible at the incision 304 without being kinked or buckled inside the lumen 118.

While embodiments have been particularly shown and described, it will be understood by those skilled in the art that various other changes in the form and details may be made therein without departing from the spirit and scope of the invention.

What is claimed is:

1. A tunneling tool for implanting a lead extension, comprising:
    a tool body having a lumen sized to allow passage of a body and proximal and distal connectors of the lead extension;
    a handle attached to a proximal end of the tool body, the handle having a passageway that is sized to receive a portion of the body of the lead extension;
    a distal cap that is removably attached to a distal end of the tool body; and
    a tracker tube having a distal compartment sized to receive and carry the distal connector of the lead extension while the body of the lead extension is present within the lumen and the passageway, the tracker tube including a distal body forming a distal end of the distal compartment, the distal body being movable within and relative to the tool body, the tracker tube being contained within the lumen of the tool body and with the distal compartment being positioned in proximity to the distal end of the tool body, and with a portion of the tracker tube forming the distal compartment having an external lateral width that is larger than an external lateral width of a remainder of the tracker tube that extends longitudinally from the distal compartment in a proximal direction and with an external lateral width of the distal body being at least as large as the external lateral width of the portion of the tracker tube forming the distal compartment.

2. The tunneling tool of claim 1, wherein the distal cap has threads that engage threads of the distal end of the tool body.

3. The tunneling tool of claim 1, wherein the distal cap has a conical interior and exterior shape and wherein the distal body of the tracker tube includes a conical distal end that is positioned within the conical interior shape of the distal cap.

4. The tunneling tool of claim 1, wherein the tracker tube has a longitudinal slot.

5. A system, comprising:
    a lead extension having a lead body, a proximal connector, and a distal connector;
    a tool body having a lumen with a portion of the body and the proximal connector being present within the tool body;
    a handle attached to a proximal end of the tool body, the handle having a passageway with a portion of the body of the lead extension being positioned in the passageway;
    a distal cap that is removably attached to a distal end of the tool body; and
    a tracker tube having a distal compartment where the distal connector of the lead extension is positioned while the body of the lead extension is present within the lumen and passageway, the tracker tube including a distal body forming a distal end of the distal compartment, the distal body being movable within and relative to the tool body, the tracker tube being contained within the lumen of the tool body and with the distal compartment being positioned in proximity to the distal end of the tool body, and with a portion of the tracker tube forming the distal compartment having an external lateral width that is larger than an external lateral width of a remainder of the tracker tube that extends longitudinally from the distal compartment in a proximal direction and with an external lateral width of the distal body being at least as large as the external lateral width of the portion of the tracker tube forming the distal compartment.

6. The system of claim 5, wherein the distal cap has threads that engage threads of the distal end of the tool body.

7. The system of claim 5, wherein the distal cap has a conical interior and exterior shape and wherein the tracker tube includes a conical distal end that is positioned within the conical interior shape of the distal cap.

8. The system of claim 5, wherein the tracker tube has a longitudinal slot.

\* \* \* \* \*